(12) United States Patent
Ciliberto et al.

(10) Patent No.: US 6,929,782 B1
(45) Date of Patent: Aug. 16, 2005

(54) DISSOLUTION TEST SAMPLE HOLDER

(75) Inventors: Cynthia M. Ciliberto, Port Deposit, MD (US); Kenneth M. Feld, Chalfont, PA (US); Donna M. Heren, Yardley, PA (US)

(73) Assignee: Aventis Pharmaceuticals Inc., Bridgewater, NJ (US)

( * ) Notice: Subject to any disclaimer, the term of this patent is extended or adjusted under 35 U.S.C. 154(b) by 0 days.

(21) Appl. No.: 09/890,484

(22) PCT Filed: Feb. 4, 2000

(86) PCT No.: PCT/US00/03003

§ 371 (c)(1),
(2), (4) Date: Dec. 31, 2001

(87) PCT Pub. No.: WO00/46597

PCT Pub. Date: Aug. 10, 2000

Related U.S. Application Data
(60) Provisional application No. 60/118,827, filed on Feb. 5, 1999.

(51) Int. Cl.[7] .................................................. B01L 9/00
(52) U.S. Cl. .................... 422/104; 422/99; 422/101; 422/102; 436/178; 436/179; 73/53.01; 73/64.56
(58) Field of Search ........................ 422/68.1, 99, 101, 422/104, 264; 436/178, 179; 73/53.01, 64.55, 432.1

(56) References Cited

U.S. PATENT DOCUMENTS

| | | | | |
|---|---|---|---|---|
| 3,801,280 A | * | 4/1974 | Shah et al. ................ 23/230 R |
| 3,802,272 A | * | 4/1974 | Bischoff et al. ........... 73/432 R |
| 4,274,286 A | * | 6/1981 | Gioia ........................... 73/432 |
| 4,464,340 A | * | 8/1984 | Lennox, Jr. et al. ......... 422/103 |
| 4,578,244 A | * | 3/1986 | Cosgrove, Jr. et al. ....... 422/65 |
| 4,681,858 A | * | 7/1987 | Chaudhari et al. .......... 436/165 |
| 4,856,909 A | * | 8/1989 | Mehta et al. ................ 366/208 |
| 5,011,662 A | * | 4/1991 | Noormohammadi et al. .......................... 422/68.1 |
| 5,108,710 A | * | 4/1992 | Little et al. ................. 422/104 |
| 5,407,567 A | * | 4/1995 | Newhard .................. 210/198.1 |
| 5,412,979 A | * | 5/1995 | Fassihi ...................... 73/53.01 |
| 5,476,116 A | * | 12/1995 | Price et al. .................. 137/268 |
| 5,589,649 A | * | 12/1996 | Brinker et al. ................ 73/866 |
| 5,816,701 A | * | 10/1998 | Martin et al. ............... 366/208 |
| 5,958,778 A | * | 9/1999 | Kidd ........................... 436/45 |
| 6,336,739 B1 | * | 1/2002 | Lee ............................ 366/143 |
| 6,497,157 B1 | * | 12/2002 | Viegas et al. ................. 74/866 |

OTHER PUBLICATIONS

"Automated Dissolution Testing of Topical Drug Formulations Using Franz Cells and HPLC Analysis", (Li and Rahn) *Pharmaceutical Technology*, vol. 9, No. 10, 1992.

(Continued)

*Primary Examiner*—Jill Warden
*Assistant Examiner*—Dwayne K Handy
(74) *Attorney, Agent, or Firm*—Synnestvedt & Lechner LLP

(57) ABSTRACT

A dissolution test sample holder for testing topical formulations for dermal and/or transdermal drug delivery is disclosed. The holder has a cylinder tubular body with an end cap removably attached to one end. The end cap has a peripheral wall which frictionally engages the body to hold the end cap in place. A flange extends perpendicularly from the peripheral wall inwardly defining an aperture in the end cap and providing a support surface for a membrane held within the end cap. A ring is positioned within the end cap on the membrane, the membrane being sandwiched between the ring and the support surface. The ring protects the membrane by preventing contact between it and the body and provides a volume for holding the test sample in contact with the membrane.

17 Claims, 3 Drawing Sheets

OTHER PUBLICATIONS

"In Vitro Release of Phenol from Ointment Formulations", (Segers, Zatz & Shah) *Pharmaceutical Technology,* Jan. 1997.

"Microdialysis Sampling for the Investigation of Dermal Drug Transport", (Ault, Lunte, Meltzer & Riley) *Pharmaceutical Research,* vol. 9, No. 10, 1992.

VanKel "Enhancer Cell" Information Booklet by VanKel Technology Group.

"In Vitro Release of Nitroglycerin from Topical Products by Use of Artificial Membranes", *Journal of Pharmaceutical Sciences,* (Wu, Shiu, Simmons, Bronaugh & Skelly) vol. 81, No. 12, Dec. 1992.

Hanson Research "TDOC–015 and SVK–150F" Operation Manual 65–190–027 by Hanson Research Corporation.

"Comparison of Transdermal Diffusion of Hydrocortisone using the Traditional 'Franz Cell' Apparatus and the New 'Enhancer Cell'" (Sanghvi & Collins) Dúquesne University School of Pharmacy, Pittsburgh, Pennsylvania 15282–1504.

"A Comparison of Two Transdermal Diffusion Apparatuses: A Brief Communication", (Ritschel & Barkhaus) *Meth and Find Exptl Clin Pharmacol,* 1987; 9(10): 673–676.

Hanson Research "Domestic USA Price Catalog", Oct., 1996 by Hanson Research Corporation.

"Physical Tests", *U.S. Pharmacopeia,* sections 711, 721 and 724.

* cited by examiner

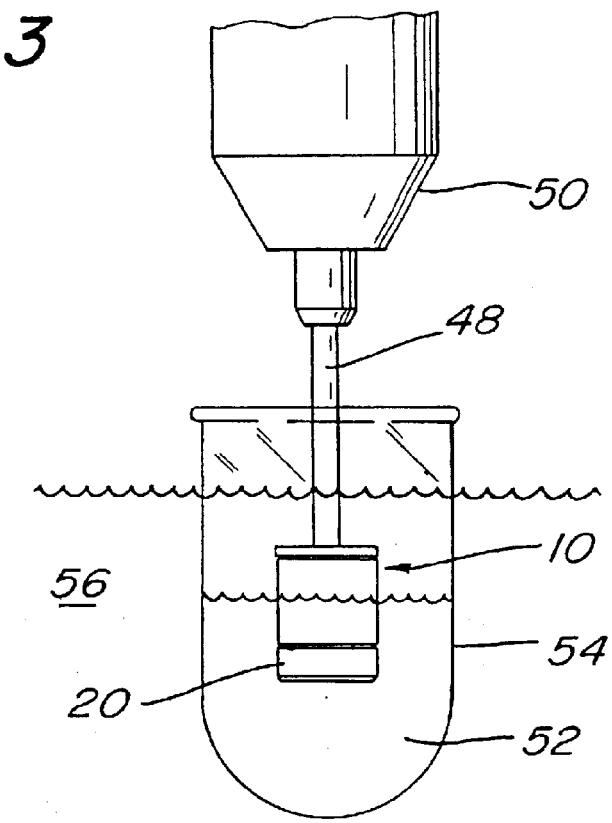
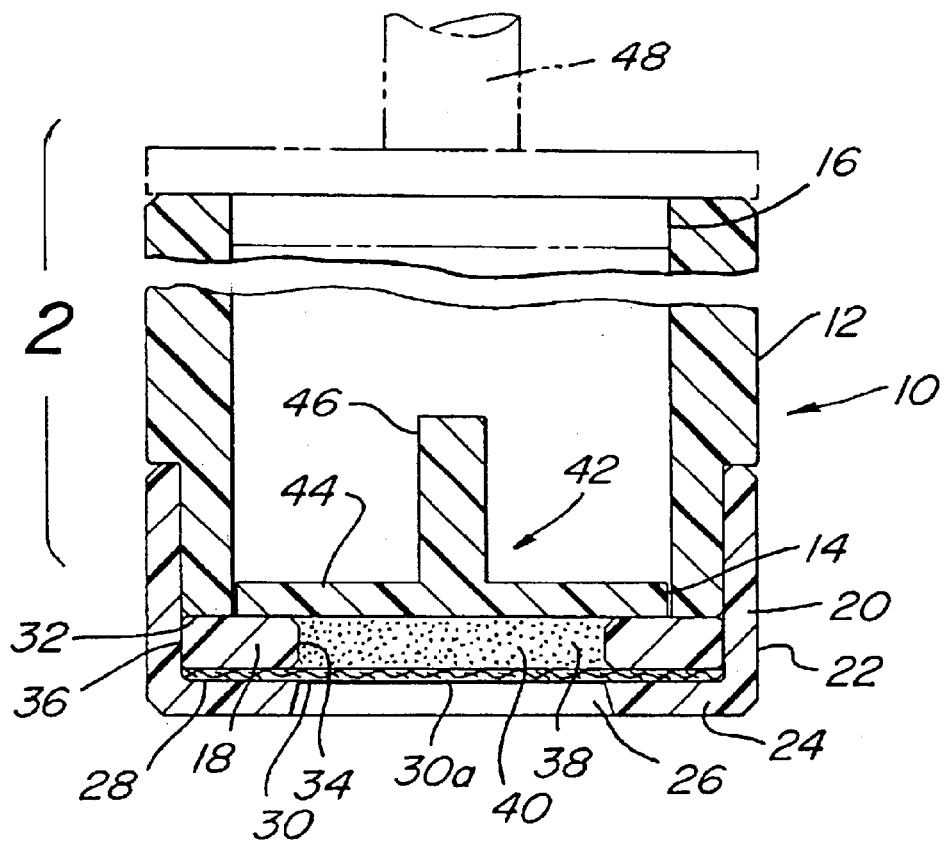

DISSOLUTION TEST SAMPLE HOLDER

This application claims benefit of 60/118,827 filed Feb. 5, 1999.

FIELD OF THE INVENTION

This invention is a device for holding a test sample during dissolution and/or release testing and is especially suited for holding viscous topical formulations used for transdermal and dermal drug delivery.

BACKGROUND OF THE INVENTION

Topical formulations, including ointments, creams, lotions, pastes, oils and gels, are used in the dermal and transdermal (through the skin) delivery of active drugs such as, for example, hydrocortisone and nitroglycerin to sites of action in the body.

Topical application of a drug is advantageous because it allows localized delivery of the therapeutic agent directly to the desired site, thus, increasing bioavailability (the extent to which a drug reaches its site of action), reducing drug side effects and loss of therapeutic efficiency and increasing patient compliance.

An important parameter in the development of dermal and transdermal drug delivery formulations is the rate at which the active drug is delivered. This parameter is measured in vitro (literally "in glass", meaning in the laboratory as opposed to in the living body) by drug release and/or dissolution testing. The United States Pharmacopeia specifies FDA approved standards for equipment and procedures used for dissolution testing.

It has been convention that a sample of the formulation, be it a cream, lotion, ointment, gel or other medium containing the drug or active agent, is placed on one side of a permeable membrane which simulates the barrier, presented by the skin, between the drug and the site of action. The membrane could be formed from actual skin taken from a laboratory animal, or a synthetic material such as polysulfone, acrylic polymer, glass fiber or PTFE to cite a few examples. The side of the membrane opposite the test sample is brought into contact with a liquid receptor media, and the drug or other active agent in the formulation diffuses through the membrane and dissolves into the receptor media. The concentration of the drug in the receptor media is measured periodically over time to establish the rate at which it is delivered into the media, thus, providing an indication of its delivery rate in actual use.

There are various devices currently available to hold the test sample during dissolution testing, and all of them suffer from one or more serious disadvantages. For example, some of the devices are complicated, having many interfitting parts which can be difficult and tedious to assemble. Assembly must be done by experienced technicians using great care to avoid puncturing, tearing or wrinkling the delicate membranes held in the devices. The devices are often loaded with the test sample before they are fully assembled, thus, preventing simple visual checks from being performed after assembly to ensure that the proper quantity of sample has been loaded and that the entire membrane surface is covered by the sample. In use, the devices are typically fully immersed in the vessel holding the receptor media with the membrane located facing upward at the top of the device. In this configuration, gravity works to pull the test sample out of contact with the membrane, air pockets can form adjacent to the membrane preventing contact between sample and membrane and causing variability of test measurements. This configuration also results in a "dead volume" of the receptor media forming under the device, the media in the "dead volume" being stagnant and not participating in the dissolution of the sample and, thus, being a source of inaccuracy in the measurements.

Clearly, there is a need for an improved test sample holder for dissolution testing which is simple in construction, is easy to assemble, minimizes the potential for damage to the membrane, allows for visual observation of the test sample, avoids the creation of dead volumes of receptor media or air pockets and is useable with standard United States Pharmacopeia dissolution equipment and procedures.

SUMMARY AND OBJECTS OF THE INVENTION

The invention is a dissolution test sample holder immersible within a liquid for measuring the release or dissolution rate of a test sample in the liquid. The test sample is dispensed into the liquid by diffusion through a porous membrane mounted within the holder.

The holder is formed by a tubular body having opposed ends, at least one of the ends being open. An end cap is removably attached to the open end. The end cap has a peripheral side wall coaxially interengaged with the body. Frictional forces between the side wall and the body hold the end cap removably to the body. An interference fit between the end cap and the body causes the friction and results in a seal between the side wall and the body. A flange extends substantially perpendicularly inwardly of the side wall and forms a surface within the end cap for supporting the porous membrane, the flange surrounding and defining an aperture through the end cap. The membrane is positionable on the surface and covers the aperture. The test sample is positionable within the end cap on the membrane.

The end of the body to which the end cap is attached is immersible to bring the membrane into contact with the liquid, thereby allowing the test sample to diffuse though the porous membrane and dissolve in the liquid.

When particularly delicate or thin membranes are to be used, it is preferable to include a ring sized to fit coaxially within the end cap. The ring is positioned on top of the membrane, the membrane being sandwiched between the ring and the support surface. The ring has a predetermined thickness and an inner perimeter defining a volume holding the test sample in contact with the membrane. When the holder is assembled, the body frictionally interfits within the end cap side wall and has an end surface engaging the ring and clamping the membrane between the ring and the support surface. The ring protects the delicate membrane from tearing or wrinkling by preventing direct contact between the body and the membrane.

In the preferred embodiment of the test sample holder, the tubular body and the end cap are cylindrical in shape, the aperture is circular and has a predetermined diameter, and the ring has circular inner and outer perimeters. In this embodiment, the ring inner diameter is substantially equal to the diameter of the aperture. This helps confine the test sample to the wetted area of the membrane, thus, ensuring that all of the sample is available for dissolution into the liquid. Varying the ring inner diameter as well as the ring thickness allows the volume of the test sample to be controlled as desired within the size limits of the end cap and body. In order to provide a membrane support surface of practical size, the end cap aperture diameter is smaller than an inner diameter of the body.

Due to its construction, the test sample holder according to the invention allows the test sample to be loaded after the holder has been assembled. This provides an opportunity to visually inspect the loaded holder and ensure that the correct amount of sample has been loaded, that there are no air bubbles or other voids in the sample diminishing the membrane wetted surface and that the membrane has not been damaged by the assembly or loading of the holder.

It is sometimes necessary to take steps to prevent the test sample from evaporating during the dissolution testing. Evaporation of the test sample will cause inaccurate test results and should be avoided. Evaporation may be caused when the test is conducted at elevated temperatures or when the test duration is long due to low dissolution rates. To prevent evaporation, a sample cover is used. The sample cover is formed by a disk having a diameter sized to slidingly interfit coaxially within the body and seat on the ring. When seated, the disk covers the test sample held within the inner perimeter of the ring.

It is desired to provide agitation of the liquid in the vicinity of the membrane to promote mixing of the test sample to maintain sink conditions (i.e., always having a very low concentration of the active agent). Agitation is provided by having an opening in the body at the opposite end from the end cap, the opening being sized to accept a rotatable shaft in frictional interengagement. Preferably, the shaft is coaxial with the body and rotates it with the end cap end immersed within the liquid to promote dissolution of the test sample into the liquid.

The invention is used in a method of dissolution and/or release testing of a test sample in a liquid. Preferably, the method comprises the steps of:

(a) providing a tubular body having opposed open ends;

(b) providing an end cap removably attachable to one of the ends, the end cap having a peripheral side wall coaxially interengagable with the body and a flange extending substantially perpendicularly inwardly of the side wall and forming a support surface within the end cap, the flange surrounding and defining an aperture through the end cap;

(c) providing a porous membrane positionable within the end cap on the support surface and covering the aperture;

(d) positioning the membrane on the support surface covering the aperture;

(e) attaching the end cap to the one end of the body by engaging the body with the peripheral wall;

(f) loading the test sample onto the membrane through the opposite open end of the body;

(g) immersing the one end of the body into the liquid thereby wetting said membrane; and (h) measuring the concentration of the test sample in the liquid periodically.

When necessitated by the use of a thin or delicate membrane, the method also includes the steps of:

(i) providing a ring sized to fit coaxially within the end cap contiguous with the membrane, the ring having a predetermined thickness and an inner perimeter defining a volume holding the test sample in contact with the membrane;

(j) positioning the ring on the membrane coaxially within the end cap before the body and the end cap are interengaged, the membrane being sandwiched between the support surface and the ring.

When the ring is used, the loading step comprises loading the test sample onto the membrane within the inner perimeter of the ring.

When it is desired to agitate the liquid to promote dissolution the following steps are also included:

(k) attaching the other end of the tubular body (the end opposite from the end cap) coaxially to a rotatable shaft; and (l) rotating the body while the one end is immersed in the liquid to promote dissolution of the test sample.

It is an object of the invention to proved a dissolution test sample holder which will allow accurate measurements of the dissolution and/or release rate of a test sample to be taken.

It is another object of the invention to provide a test sample holder which will provide consistent and repeatable dissolution and/or release rates of a test sample with a minimum of test variability.

It is a further object of the invention to provide a test sample holder which is easy to assemble and load with the test sample.

It is yet another object of the invention to provide a test sample holder wherein the test sample is exposed to the entire wetted surface of the membrane.

It is still another object of the invention to provide a test sample holder wherein the test sample diffuses through the membrane by gravity.

It is again another object of the invention to provide a test sample holder wherein the volume of the test sample can be easily varied.

It is a further object of the invention to provide a test sample holder capable of using delicate membranes without damaging them.

It is again a further object of the invention to provide a test sample holder wherein the test sample can be visually inspected after the holder has been assembled and the test sample has been loaded.

It is yet another object of the invention to provide a test sample holder which can be rotated to provide agitation to promote the dissolution of the test sample.

It is again another object of the invention to provide a test sample holder which can be used with standard dissolution equipment and procedures as specified in the United States Pharmacopeia.

It is a further objective of the invention to provide a method for using a test sample holder according to the invention to accurately, reliably, and repeatably measure the dissolution and/or release rate of a test sample.

These and other objects can be discerned from a consideration of the following drawings and detailed description of the invention.

BRIEF DESCRIPTION OF THE DRAWINGS

FIG. 2 is a cross sectional side view of the test sample holder shown in FIG. 1, the holder being shown assembled and on an enlarged scale;

FIG. 3 is a side view of the test sample holder shown in FIGS. 1 and 2 in operation, FIG. 3 being on a reduced scale.

DETAILED DESCRIPTION OF THE PREFERRED EMBODIMENT

Figure 1:
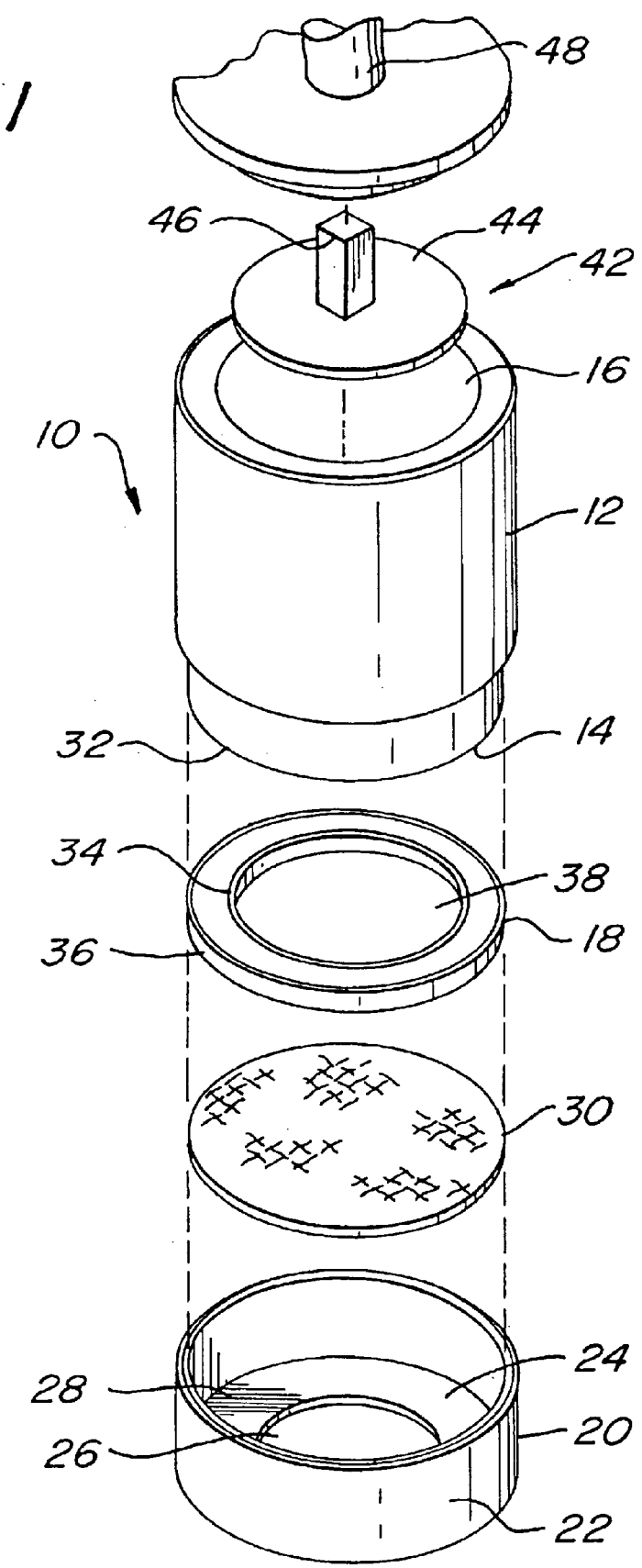
FIG. 1 is an exploded perspective view of a test sample holder according to the invention.

FIG. 1 shows an exploded isometric view of an in vitro dissolution test sample holder 10 according to the invention. Sample holder 10 comprises a tubular body 12 having opposed open ends 14 and 16, a ring 18 and an end cap 20.

End cap 20 has a peripheral side wall 22 coaxially interengagable with the body 12 at open end 14, and a flange 24 which extends substantially perpendicularly inwardly to define an aperture 26 through the end of the end cap. Cylindrical and circular shapes for the body, ring, end cap and apertures are preferred for ease of manufacture and assembly of the holder 10.

Flange 24 forms a support surface 28 within the end cap to support a porous membrane 30 which is placed within the end cap in overlying relation covering aperture 26. The diameter of aperture 26 is smaller than the inner diameter of body 12 to provide a membrane support surface of practical size. Ring 18 interfits coaxially within end cap 20 on top of membrane 30, the membrane being sandwiched between ring 18 and support surface 28 as seen in the cross-sectional view of FIG. 2. Synthetic membranes having pore sizes on the order of 0.45 microns have been found useful in dissolution testing although membranes of natural material, such as skin harvested from laboratory animals are also contemplated.

End cap 20 removably interengages tubular body 12, the end cap being retained to the tubular body, preferably by a friction or interference fit between the peripheral side wall 22 and the tubular body. It is preferred to have end cap 20 receive the body 12 as shown in FIG. 2 allowing the cap to be manually gripped and easily removed from the body. The frictional interengagement between side wall 22 and body 12 forms a seal keeping liquid receptor media out of the body when the holder is immersed as described below. Frictional interengagement of the end cap and the body eliminates the need for O-rings and other types of seals, thus, simplifying the design of the holder.

The tubular body has an end surface 32 at open end 14 which engages ring 18 and compresses it against the membrane 30. The membrane is, thus, clamped between flange 24 and ring 18 by the compressive force between the end cap and the tubular body.

Ring 18 has an inner perimeter 34 which is preferably sized and shaped to match the size and shape of aperture 26 as shown in FIG. 2. The ring also has a predetermined thickness 36. As best seen in FIG. 2, the thickness 36 and perimeter 34 define a sample holding volume 38 where a sample 40 of the formulation to be tested is placed.

A sample cover 42 is provided to prevent the sample from evaporating and leaving a residue during testing. Evaporation is a concern for example, during dissolution testing at elevated temperatures, or during tests of long duration. Preferably, sample cover 42 comprises a disk 44 which is sized and shaped to easily fit coaxially within tubular body 12 and seat on top of ring 18 completely covering the holding volume 38. The sample cover has a handle 46 to facilitate manual placing of the sample cover into the tubular body.

Figure 4:
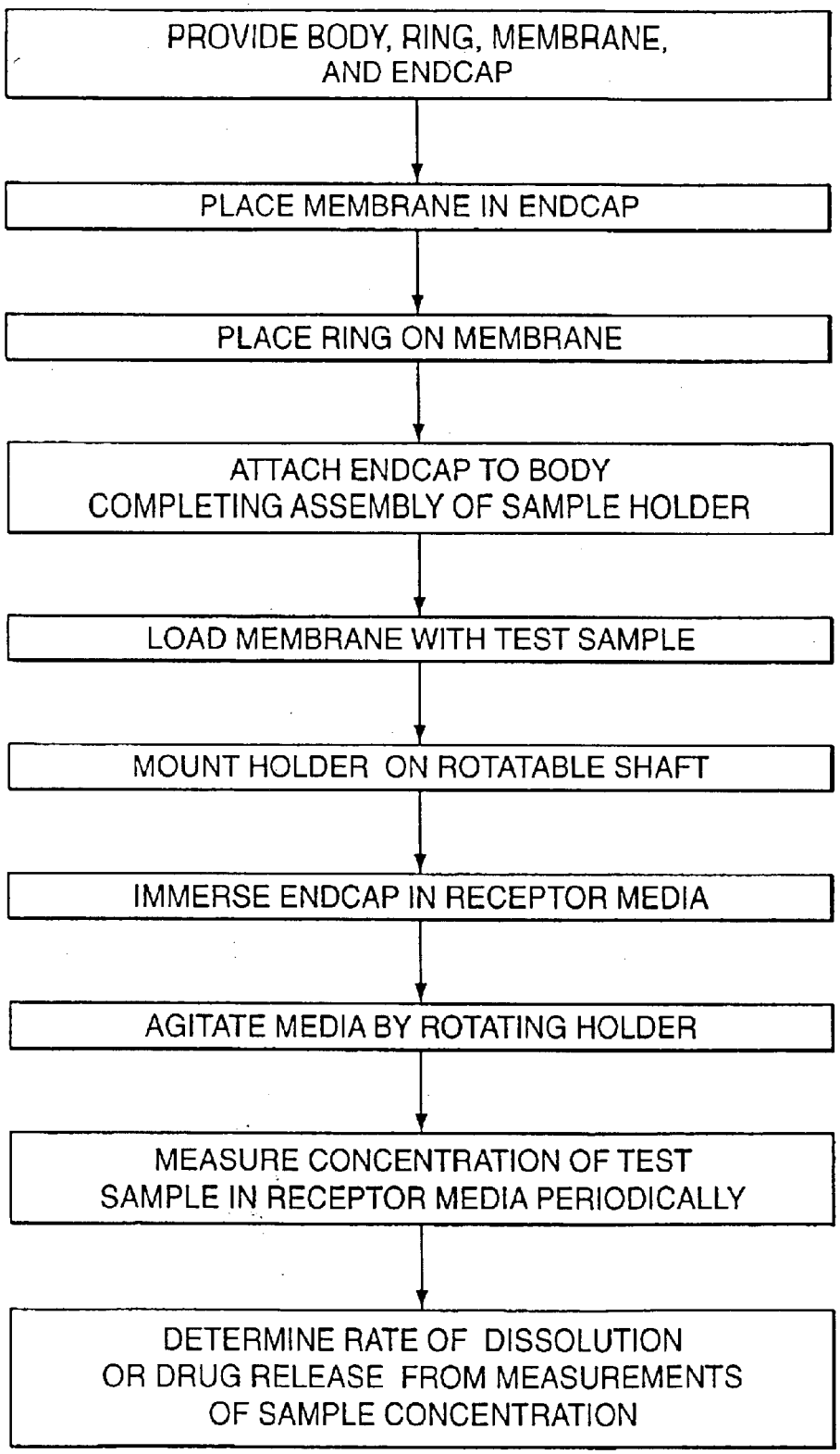
FIG. 4 is a flow chart describing a method for dissolution testing according to the invention.

FIG. 4 is a flow chart which describes a method of dissolution testing according to the invention. Briefly described, the method steps include providing the various components comprising the test sample holder, assembling the components, loading the membrane with the test sample, mounting the holder on a rotatable shaft, immersing the end cap into a receptor media, agitating the media by rotating the holder, periodically measuring the concentration of the test sample in the receptor media and determining the rate of dissolution or drug release from the concentration measurements. These steps are described in more detail below.

To assemble the sample holder 10 according to the invention, the membrane 30 is placed within end cap 20 on support surface 28 completely covering aperture 26. Ring 18 is then placed within end cap 20 on membrane 30. The end cap is interengaged with the open end 14 of tubular body 12, the peripheral side wall 22 receiving and engaging the tubular body 12 forming a seal and the tubular body end surface 32 engaging and compressing ring 18 against the membrane. Sample material 40 is then loaded into the holding volume 38 through the opposite open end 16 of body 12. The sample may be visually checked through open end 16 of body 12 to ensure that it completely covers the portion of membrane 30 beneath the holding volume 38 without any air pockets or other voids. If desired, the sample cover 42 is placed within the tubular body 12 after visual inspection. The sample cover seats against ring 18 and prevents evaporation of the sample during the test.

As seen in FIG. 2, the assembled sample holder 10, loaded with test sample material 40, is mounted on the end of a shaft 48 which is rotatably mounted on an armature 50 shown in FIG. 3. Preferably, open end 16 of body 12 receives the shaft, the shaft and the body interfitting in a friction or interference fit which retains the body to the shaft, yet allows it to be easily manually removed without the need for tools and separate fasteners. This affords a simple design, which is easy to use and requires few parts.

As seen in FIG. 3, the sample holder 10 is mounted on the end of rotatable shaft 48 and positioned with end cap 20 immersed in a liquid receptor media 52 contained within a vessel 54. Vessel 54 is itself immersed in a liquid bath 56 used to control the temperature of the receptor media 52. Preferably, receptor media 52 is a phosphate buffered aqueous solution having a pH which is set to simulate the conditions under which the sample will be used to dermally and/or transdermally deliver a drug or other therapeutic agent. Aperture 26 (see FIG. 2) exposes the side 30a of membrane 30 opposite the sample material 40 to the receptor media 52. Care must be taken not to trap air against the membrane during immersion of the end cap, as it is preferable that the entire exposed membrane surface 30a be wetted by and in contact with the receptor media 52 to promote the dissolution and/or release of the active agent within the test sample 40 into the receptor media 52. If required, sample holder 10 can be rotated on shaft 48 by armature 50 at a predetermined rate to agitate the receptor media and further promote dissolution by maintaining sink conditions.

As the drug or other therapeutic agent diffuses through the membrane and dissolves in the receptor media 52, a portion of the receptor media is removed from vessel 54 periodically and the concentration of the drug or therapeutic agent in the media is measured. The dissolution or drug release rate is then determined from these concentration measurements. One method of determining the rate is by generating a curve depicting the functional relation of concentration versus time from these measurements, the slope of the curve providing the dissolution rate of the sample. Preferably, the volume of the receptor media 52 is sufficiently large to keep the receptor media in a sink condition, i.e., always having a very low concentration of the active agent so as not to affect the dissolution or release rate of the sample.

Preferably, the sample holder 10 is made of a chemically stable material such as Teflon® (PTFE), stainless steel or titanium so that it will not react with the sample material or the receptor media and adversely affect the dissolution testing. It is advantageous to fabricate all of the components from the same material so that all of the parts have the same coefficient of thermal expansion. This will ensure that the parts fit together in the same relationship and maintain friction fits regardless of the temperature of the sample holder. If stainless steel or titanium is used, it is desirable to coat any points of contact between parts with Teflons to facilitate assembly of the parts by allowing them to slide easily over one another.

Arranging the sample holder with the membrane 30 at the bottom ensures that the sample material 40 will be in contact with the membrane during the testing and, thus, be available to diffuse through the membrane and dissolve in the receptor media 52. It is expected that this configuration will provide for accurate, reproducible test results with a minimum of undesired variability between tests. This is especially important for testing lotions or oils which have a relatively low viscosity as compared with creams, gels or pastes. Lotions or oils would tend to run and separate from the membrane if the sample holder were in any other orientation. Thus, not all of the sample would be available for dissolving in the receptor media, adversely affecting the test results.

Furthermore, by suspending and rotating the sample holder in vessel 54, all of the receptor media 52 will be available as a solvent, thus, eliminating stagnant "dead zones" of receptor media where effective mixing of solvent and solute does not occur. Dead zones in receptor media 52 are undesirable because they may lead to erroneous test results. Calculations of the concentration are based upon the entire volume of receptor media, but if there is a dead zone, an unknown and unquantifiable part of that volume is not participating in the test. This will introduce error into the test results.

The use of the ring 18 to hold the membrane 30 in place provides a distinct advantage over other sample holders by allowing the sample holder according to the invention to be easily assembled without damaging the membrane. Membranes tend to be delicate and easily torn, wrinkled or punctured when inserted into the sample holder. It is especially difficult to assemble sample holders in which the membrane is clamped between two parts which move relatively to one another, such as a screw cap on the end of a cylinder. By gently placing ring 18 on top of membrane 30 before placing end cap 20 onto the end of tubular body 12, the membrane is protected from any relative movement between the cap and its mating part, the tubular body.

Another advantage secured by the invention is that the sample holder is completely assembled before any sample is introduced into it. This allows the sample material 40 to be visually inspected after it is placed in the sample holding volume 38 to ensure that the material is in contact with the entire membrane beneath the holding volume, and there are no air bubbles trapped against the membrane forming an occlusion. This is unlike other sample holders in which the sample material is placed into a part of the holder which is then joined to another part, effectively blocking all access to the sample material. Allowing visual inspection of the sample material prior to the test will help ensure accurate and repeatable test results with variability reduced to a minimum.

The in vitro test sample holder according to the invention is expected to provide an improved device for dissolution testing of topical formulations for the dermal and/or transdermal delivery of drugs or other therapeutic agents. Its configuration and construction are specifically designed to avoid the problems and disadvantages associated with devices currently used for dissolution and/or release testing and should result in more accurate and reliable test results.

What is claimed is:

1. A dissolution test sample holder immersible within a liquid for measuring the dissolution or release rate of a test sample in said liquid, said holder comprising:

a tubular body having opposed ends, one of said ends being open;

an end cap removably attached to said one end, said end cap having a peripheral side wall coaxially interengaged with said body and a flange extending substantially perpendicularly inwardly of said side wall and forming a support surface within said end cap, said flange surrounding and defining an aperture through said end cap;

a porous membrane positioned within said end cap on said support surface and covering said aperture;

a ring sized to fit coaxially within said end cap contiguous with said membrane, said membrane being sandwiched between said support surface and said ring, said ring having a predetermined thickness and an inner perimeter defining a volume holding said test sample in contact with said membrane;

said one end of said body being immersible to bring said membrane into contact with said liquid, said test sample passing though said porous membrane upon immersion and dissolving in said liquid.

2. A dissolution test sample holder according to claim 1, wherein said tubular body and said end cap are cylindrical in shape, said aperture is circular and has a predetermined diameter, and said ring has circular inner and outer perimeters.

3. A dissolution test sample holder according to claim 2, wherein said end cap is removably attached to said body by friction between said side wall and said body.

4. A dissolution test sample holder according to claim 3, wherein said body forms a seal with said end cap side wall.

5. A dissolution test sample holder according to claim 3, wherein said ring has an inner diameter substantially equal to said aperture diameter and said aperture diameter is smaller than an inner diameter of said body.

6. A dissolution test sample holder according to claim 5, further comprising a sample cover formed by a disk having a diameter sized to slidingly interfit coaxially within said body and seat on said ring, said disk covering said test sample held within said inner perimeter of said ring on said membrane.

7. A dissolution test sample holder according to claim 5, wherein said body has another open end opposite said one end, said other open end being sized to accept a rotatable shaft in frictional interengagement, said shaft being coaxial with and rotating said body with said one end immersed within said liquid to promote dissolution of said test sample into said liquid.

8. A dissolution test sample holder according to claim 5, wherein said tubular body has an end surface positioned at said one end engaging said ring, said end surface compressing said ring and clamping said membrane between said ring and said support surface.

9. A dissolution test sample holder immersible within a liquid for measuring the dissolution or release rate of a test sample in said liquid, said test sample being dispensed into said liquid through a porous membrane mounted within said holder, said holder comprising:

a tubular body having opposed ends, at least one of said ends being open;

an end cap removably attached to said one end, said end cap having a peripheral side wall coaxially interengaged with said body and a flange extending substantially perpendicularly inwardly of said side wall and forming a surface within said end cap for supporting said membrane, said flange surrounding and defining an aperture through said end cap, said membrane being positionable on said surface covering said aperture, said test sample being positionable within said end cap on said membrane;

a ring sized to fit coaxially within said end cap on top of said membrane, said ring having a predetermined thickness and an inner perimeter defining a volume holding said test sample in contact with said membrane; and said one end of said body being immersible to bring said membrane into contact with said liquid, said test sample passing though said porous membrane upon immersion and dissolving in said liquid.

10. A dissolution test sample holder according to claim 9, wherein said tubular body and said end cap are cylindrical in shape, said aperture is circular and has a predetermined diameter, and said ring has circular inner and outer perimeters.

11. A dissolution test sample holder according to claim 10, wherein said one end of said body frictionally interfits within said end cap side wall and is contiguous with said ring, said ring preventing contact between said body and said membrane.

12. A dissolution test sample holder according to claim 11, wherein said ring has an inner diameter substantially equal to said aperture diameter and said aperture diameter is smaller than an inner diameter of said body.

13. A dissolution test sample holder according to claim 12, wherein the other of said ends is open and is sized to accept a rotatable shaft in frictional interengagement, said shaft being coaxial with and rotating said body with said one end immersed within said liquid to promote dissolution of said test sample into said liquid.

14. A method of dissolution testing a test sample in a liquid, said method comprising the steps of:

providing a tubular body having opposed ends, at least one of said ends being open;

providing an end cap removably attachable to said one end; said end cap having a peripheral side wall coaxially interengagable with said body and a flange extending substantially perpendicularly inwardly of said side wall and forming a support surface within said end cap, said flange surrounding and defining an aperture through said end cap;

providing a porous membrane positionable within said end cap on said support surface and covering said aperture;

positioning said membrane on said support surface covering said aperture;

loading said test sample onto said membrane;

attaching said end cap to said one end of said body;

immersing said one end of said body into said liquid thereby wetting said membrane; and measuring the concentration of said test sample in said liquid periodically.

15. A method of dissolution testing according to claim 14, further including the steps of:

providing a ring sized to fit coaxially within said end cap contiguous with said membrane, said ring having a predetermined thickness and inner perimeter defining a volume holding said test sample in contact with said membrane;

positioning said ring on said membrane coaxially within said end cap, said membrane being sandwiched between said support surface and said ring; and wherein said loading step comprises loading said test sample onto said membrane within said inner perimeter of said ring.

16. A method of dissolution testing according to claim 15, wherein the other end of said tubular body is open, said steps positioning said ring and attaching said end cap occur before said loading step, and said loading step comprises loading said test sample onto said membrane through said other open end.

17. A method of dissolution testing according to claim 16, further including the steps of attaching said other end of said tubular body coaxially to a rotatable shaft, and rotating said body while said one end is immersed in said liquid to promote dissolution of said test sample.

* * * * *